(12) United States Patent
Dae

(10) Patent No.: US 9,597,226 B2
(45) Date of Patent: *Mar. 21, 2017

(54) DEVICES AND METHODS FOR USING ENDOVASCULAR COOLING TO TREAT SEPTIC SHOCK AND OTHER DISORDERS

(71) Applicant: ZOLL Circulation, Inc., Sunnyvale, CA (US)

(72) Inventor: Michael W Dae, Belmont, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 576 days.

This patent is subject to a terminal disclaimer.

(21) Appl. No.: 13/932,743

(22) Filed: Jul. 1, 2013

(65) Prior Publication Data

US 2014/0148882 A1 May 29, 2014

Related U.S. Application Data

(63) Continuation of application No. 11/891,684, filed on Aug. 9, 2007, now Pat. No. 8,475,509.

(51) Int. Cl.
*A61F 7/12* (2006.01)
*A61F 7/00* (2006.01)

(52) U.S. Cl.
CPC .............. *A61F 7/0085* (2013.01); *A61F 7/12* (2013.01); *A61F 2007/0054* (2013.01); *A61F 2007/0093* (2013.01); *A61F 2007/126* (2013.01)

(58) Field of Classification Search
CPC ............ A61F 7/0085; A61F 2007/0054; A61F 2007/0093; A61F 2007/126
See application file for complete search history.

(56) References Cited

U.S. PATENT DOCUMENTS

| 5,174,285 | A | | 12/1992 | Fontenot |
| 5,217,019 | A | * | 6/1993 | Hughes ................. A61B 5/028 |
| | | | | 600/481 |
| 5,344,436 | A | | 9/1994 | Fontenot et al. |
| 5,383,918 | A | | 1/1995 | Panetta |
| 5,486,208 | A | | 1/1996 | Ginsburg |

(Continued)

FOREIGN PATENT DOCUMENTS

| DE | 19531935 | | 2/1997 |
| JP | 2007516782 | A | 6/2007 |

(Continued)

OTHER PUBLICATIONS

Marjut Varpula, et al.: "Mixed venous oxygen saturation cannot be estimated by central venous oxygen saturation in septic shock", Intensive Care Medicine, Springer, Berlin, DE, vol. 32, No. 9, Jul. 7, 2006, pp. 1336-134.

(Continued)

*Primary Examiner* — Kaitlyn Smith
(74) *Attorney, Agent, or Firm* — Robert D. Buyan; Stout, Uxa & Buyan, LLP (57) ABSTRACT

Apparatus, systems and methods for cooling or warming the temperature of all or a portion of the body of a human or animal subject to treat disorders including but not limited to sepsis, septic shock or other inflammatory or infectious conditions which can result in shock, hypoxia, ischemia and/or multiple organ failure in human or animal subjects.

19 Claims, 3 Drawing Sheets

(56) References Cited

U.S. PATENT DOCUMENTS

| | | | |
|---|---|---|---|
| 5,837,003 | A | 11/1998 | Ginsburg |
| 5,957,963 | A | 9/1999 | Dobak, III |
| 6,096,068 | A | 8/2000 | Dobak, III et al. |
| 6,126,684 | A | 10/2000 | Gobin et al. |
| 6,149,673 | A | 11/2000 | Ginsburg |
| 6,149,676 | A | 11/2000 | Ginsburg |
| 6,231,594 | B1 | 5/2001 | Dae |
| 6,497,721 | B2 | 12/2002 | Ginsburg et al. |
| 6,527,798 | B2 | 3/2003 | Ginsburg et al. |
| 6,572,638 | B1 | 6/2003 | Dae et al. |
| 6,582,457 | B2 | 6/2003 | Dae et al. |
| 6,607,517 | B1 | 8/2003 | Dae |
| 6,610,083 | B2 | 8/2003 | Keller et al. |
| 6,620,188 | B1 | 9/2003 | Ginsbur et al. |
| 6,685,733 | B1 | 2/2004 | Dae et al. |
| 6,695,874 | B2 | 2/2004 | Machold et al. |
| 6,702,783 | B1 | 3/2004 | Dae |
| 6,702,839 | B1 | 3/2004 | Dae et al. |
| 6,786,916 | B2 | 9/2004 | Noda et al. |
| 6,887,263 | B2 | 5/2005 | Bleam et al. |
| 7,008,444 | B2 | 3/2006 | Dae et al. |
| 7,217,282 | B2 | 5/2007 | Ginsburg et al. |
| 7,258,662 | B2 | 8/2007 | Machold et al. |
| 7,318,834 | B2 | 1/2008 | Njemanze |
| 7,494,504 | B2 | 2/2009 | Ginsburg et al. |
| 7,666,215 | B2 | 2/2010 | Callister et al. |
| 7,771,460 | B2 | 8/2010 | Ginsburg et al. |
| 7,806,915 | B2 | 10/2010 | Scott et al. |
| 7,963,986 | B2 | 6/2011 | Machold et al. |
| 8,231,664 | B2 | 7/2012 | Kulstad et al. |
| 8,475,509 | B2* | 7/2013 | Dae .................. A61F 7/0085 607/104 |
| 2002/0111657 | A1* | 8/2002 | Dae .................. A61F 7/123 607/113 |
| 2002/0120314 | A1* | 8/2002 | Evans .................. A61F 7/12 607/96 |
| 2003/0088299 | A1 | 5/2003 | Magers et al. |
| 2003/0088300 | A1 | 5/2003 | Vester |
| 2004/0039431 | A1 | 2/2004 | Machold et al. |
| 2004/0087606 | A1* | 5/2004 | Voorhees .......... A61K 31/403 514/282 |
| 2004/0116988 | A1 | 6/2004 | Hammack et al. |
| 2004/0214792 | A1 | 10/2004 | Mink |
| 2005/0177212 | A1* | 8/2005 | Njemanze .......... A61F 7/12 607/104 |
| 2006/0030910 | A1 | 2/2006 | Ginsburg |
| 2007/0043409 | A1 | 2/2007 | Brian et al. |
| 2007/0150033 | A1* | 6/2007 | Johnson .......... A61F 7/106 607/114 |
| 2008/0027523 | A1 | 1/2008 | Behringer et al. |
| 2008/0091253 | A1 | 4/2008 | Hammack et al. |
| 2009/0043366 | A1 | 2/2009 | Dae |
| 2009/0182400 | A1 | 7/2009 | Dae et al. |
| 2009/0198311 | A1 | 8/2009 | Johnson et al. |
| 2010/0198319 | A1 | 8/2010 | Arad |
| 2010/0324635 | A1 | 12/2010 | Kreck |
| 2011/0208276 | A1* | 8/2011 | Machold .......... A61F 7/12 607/104 |
| 2011/0282418 | A1* | 11/2011 | Saunders .......... A61B 17/7002 607/105 |
| 2013/0317580 | A1* | 11/2013 | Simon .......... A61N 1/40 607/115 |
| 2014/0155965 | A1* | 6/2014 | Kulstad .......... A61F 7/123 607/105 |

FOREIGN PATENT DOCUMENTS

| | | |
|---|---|---|
| WO | 00/10494 | 3/2000 |
| WO | 01/10323 | 2/2001 |
| WO | 02/07793 | 1/2002 |

OTHER PUBLICATIONS

Stephen Trzeciak, et al.: "Serum lactate as a predictor of mortality in patients with infection", Intensive Care Medicine, Springer, Berlin, DE, vol. 33, No. 6, Mar. 13, 2007, pp. 970-977.

Office Action Dated Apr. 1, 2014 in corresponding European Patent Application No. 08782691.3.

Hagen, et al., "Urinary Lactate Excretion to Monitor the Efficacy of Treatment of Type I Glycogen Storage Disease", 1: Mol Genet. Metab., vol. 70, No. 3, pp. 189-95, 2000.

International Search Report and The Written Opinion in reference to PCT/US 08/72677, International Searching Authority, dated Nov. 19, 2008.

Markus Lins, et al., "Reversible Electrocardiographic Changes in Hypothermia", Zeitschrift fur Kardiologie, vol. 93, No. 8, pp. 630-33, Aug. 2004.

Van der Linden, et al., "Conjunctival Oxygen Tension Monitoring in Experimental Septic Shock", Journal of Clinical Monitoring and Computing, vol. 6, No. 1, pp. 37-43, 1989.

Sergio L. Zanotti Cavazzoni and R. Phillip Dillinger, "Hemodynamic Optimization of Sepsis-Induced Tissue Hypoperfusion", Critical Care 2006, vol. 10, Suppl 3.

Robert a. Balk, M.D., "Severe Sepsis and Septic Shock", Critical Care Clinics, vol. 16, No. 2, Apr. 2000, pp. 179-192.

Romanovsky et al., "Fever and hypothermia: two adaptive thermoregulatory responses to systemic inflammation", Medical Hypothesis (1998) vol. 50, pp. 219-226.

Villar et al, "Effects of induced hypothermia in patients with septic adult respiratory distress syndrome", Resuscitation vol. 26 (1993), pp. 183-192.

Judith S. Hochman, MD, "Cardiogenic Shock Complicating Acute Myocardial Infarction", Circulation 2003; 107: 2998-3002.

Shun Kohsaka, MD, et al., "Systemic Inflammatory Response Syndrome After Acute Myocardial Infarction Complicated by Cardiogenic Shock", Arch Intern Med. 2005; 165:1643-1650.

Scumpia et al., "Hypothermia Induces Anti-Inflammatory Cytokines and Inhibits Nitric Oxide and Myeloperoxidase-Mediated Damage in the Hearts of Endotoxemic Rats", Chest 2004; 125:1483-1491 (The Cardiopulmonary and Critical Care Journal).

Taniguchi et al, "Effects of Hypothermia on Mortality and Inflammatory Responses to Endotoxin-Induced Shock in Rats", Clinical and Diagnostic Laboratory Immunology, vol. 10, No. 5, Sep. 2003, pp. 940-943.

Supplementary European Search Report, EP 08782691, mailed Jun. 28, 2012.

L'Her, E., et al., Effects of Mild Induced Hypothermia During Experimental Sepsis; Critical Care Medicine, 34(10) : 2621-2623 (Oct. 2006).

Remick, D.G. et al., Hypothermia and Sepsis; Frontiers in Bioscience, 11, 1006-1013 (Jan. 1, 2006).

Office Action Dated Nov. 4, 2014 in corresponding Japanese Patent Application No. 2013-253416.

* cited by examiner

DEVICES AND METHODS FOR USING ENDOVASCULAR COOLING TO TREAT SEPTIC SHOCK AND OTHER DISORDERS

RELATED APPLICATION

This is a continuation of copending U.S. patent application Ser. No. 11/891,684, now U.S. Pat. No. 8,475,509, filed Aug. 9, 2007, the entire disclosure of which is expressly incorporated herein by reference.

FIELD OF THE INVENTION

This invention relates generally to methods for medical treatment and more particularly to the use of endovascular heat exchange devices to treat sepsis, septic shock or other disorders.

BACKGROUND OF THE INVENTION

It is often desirable to warm or cool all or a portion of the body of a human or animal subject. For example, it is sometimes desirable to cool a febrile patient or to warm a hypothermic patient. Also, for example, it is sometimes desirable to induce therapeutic hyperthermia or hypothermia for the purpose of treating a disorder.

Sepsis is a systemic inflammatory response and impaired circulation to provide blood and oxygen to vital organs of the body. Sepsis can result from microbial infections as well as non-infectious causes such as hemorrhagic shock, immune-mediated organ injury, ischemia, multiple trauma, tissue injury and the administration of inflammatory cytokines during cancer chemotherapy. The term "septicemia" refers to sepsis that results from microbes that are identified in circulating blood.

Patient's suffering from sepsis typically display two or more of the following symptoms:
  fever or hypothermia
  tachycardia (e.g., heart rate >90 beats per minute)
  tachypnea (e.g., respiratory rate >20 breaths per minute or a $PaCO_2$ of less than 32 mm Hg
  leukocytosis (e.g., WBC >12,000/$mm^3$), leucopenia (e.g., WBC <4,000/$mm^3$ or bandemia (e.g., >10 percent immature (band) forms).

Many patients suffering from sepsis also exhibit hypotension after an initial fluid challenge as well as a confused mental state.

In the United States alone, it has been estimated that sepsis causes the hospitalization of over 700,000 people per year, with a mortality rate of approximately 30%. In severe cases, sepsis can result in life threatening septic shock. About 45 percent of patients with sepsis progress to septic shock. In sepsis cases that progress to septic shock, the patient's circulation fails to supply enough blood and oxygen to vital organs, such as the kidneys and the brain. Septic shock remains a significant cause of death in the United States. Moreover, the incidence of sepsis and septic shock is on the rise. Such rise in the incidence of sepsis and septic shock is believed to be due to the growing elderly population, performance of increasing numbers of major surgical procedures, increased use of immunosuppressive and chemotherapeutic agents, increased prevalence of chronic debilitating conditions, increased use of invasive or implantable medical devices and increases in antibiotic resistant microbes.

Infections originating almost anywhere in the body can cause sepsis and, potentially, septic shock. Most cases of septic shock arise from infections that have originated in the lungs, kidney, or gastrointestinal tract. In some cases, the original source of the infection cannot be identified.

Septic shock can result in death. Even patients who survive septic shock sometimes suffer irreversible damage to the lungs, heart, kidneys, brain, and other organs due to the may occur.

There remains a need in the art for the development of new therapies for sepsis, septic shock and other inflammatory or infectious conditions which can result in shock, hypoxia and/or ischemia.

SUMMARY OF THE INVENTION

In accordance with one aspect of the present invention, there are provided methods for treating or preventing sepsis, septic shock or systemic inflammation in a human or animal subject in whom there has been established a diagnosis or clinical impression that the subject suffers from or is likely to develop sepsis, septic shock or other systemic inflammation. Such methods generally comprise the steps of placing a heat exchange apparatus in heat exchange proximity to blood that flows through the subject's vasculature and using the heat exchange apparatus to cool at least a portion of the subject's body to a temperature below about 35° C.

Further in accordance with the present invention, there are provided systems for treating sepsis, septic shock or other inflammatory conditions, such systems generally comprising a) a heat exchange catheter that is insertable into the subject's vasculature so as to exchange heat with blood flowing through the subject's vasculature thereby raising or lowering the subject's body temperature, b) a controller that is programmed to cause, or which receives operator commands to, i) cause the heat exchange catheter to lower the subject's body temperature to lowered temperature, ii) maintain said lowered temperature for a first period of time and iii) subsequently cause the heat exchange catheter to rewarm the subject's body temperature and c) at least one sensor that measures or monitors, during rewarming of the subject's body temperature, at least one variable that indicates whether further hypothermia is desirable, said sensor generating a signal representative of said at least one variable. The signal(s) from the sensor are transmitted to the controller and the controller is further programmed to take remedial action (e.g., to continue rewarming, maintain at the current temperature or again cool the subject's body temperature, in response to a signal(s) received from the sensor during rewarming.

Still further in accordance with the present invention, there are provided general methods for warming or cooling all or a portion of the body of a human or animal subject to treat a disorder, wherein such methods comprise the steps of (A) inserting a heat exchange catheter into the subject's vasculature, (B) using the heat exchange catheter to warm or cool blood flowing through the subject's vasculature, thereby resulting in warming or cooling of all or a portion of the subject's body (C) monitoring at least one symptom or clinical variable related to the disorder; and (D) controlling at least one operational variable selected from i) the rate of warming or cooling of blood flowing through the subject's vasculature and ii) the temperature to which the subject's body or body portion is warmed or cooled, in response to the monitored symptom or clinical variable. Such method may be used, for example, to selectively cool or warm a subject to a body temperature at which some symptom or clinical variable associated with the disorder has adequately subsided or diminished, thereby indicating that the therapeutic effect of the cooling or warming has been achieved. The present invention further includes systems for carrying out such methods, wherein the system comprises i) a heat exchange catheter that is insertable into the subject's vasculature and useable to warm or cool blood flowing through the subject's vasculature, thereby warming or cooling all or a portion of the subject's body, ii) a monitor (e.g., a sensor) for monitoring the symptom or clinical variable related to the disorder and iii) a controller which receives signals from the monitor, such monitor being programmed and operative to control at least one operational variable (e.g., the rate of warming or cooling of blood flowing through the subject's vasculature or the temperature to which the subject's body or body portion is warmed or cooled) in response to the monitored symptom or clinical variable.

Still further in accordance with the present invention, there are provided methods for warming or cooling all or a portion of the body of a human or animal subject, wherein such methods comprise the steps of (A) inserting a heat exchange catheter into the subject's vasculature, (B) using the heat exchange catheter to warm or cool blood flowing through the subject's vasculature, thereby resulting in warming or cooling of all or a portion of the subject's body, (C) monitoring for the occurrence of an undesirable symptom or undesirable change in a clinical variable which indicates that the rate of warming or cooling is to rapid or that the body or body part has been warmed or cooled to much and (D) altering the rate or amount of warming or cooling if the undesirable symptom or undesirable change in a clinical variable is observed. Such methods may be used, for example, to perform a controlled rewarming or recooling of a subject after some period of therapeutic hypothermia or hypothermia and to avoid rewaring or recooling too soon, too rapidly or in a manner that results in reoccurrence of the disorder for which the subject was originally being treated or the occurrence of some other untoward or undesired effect associated with the rewarming or recooling process. The present invention further includes systems for carrying out these methods, such systems comprising (i) a heat exchange catheter that is insertable into the subject's vasculature and useable to warm or cool blood flowing through the subject's vasculature, thereby warming or cooling all or a portion of the subject's body, ii) a monitor (e.g., a sensor) which monitors for the occurrence of an undesirable symptom or undesirable change in a clinical variable which indicates that the rate of warming or cooling is to rapid or that the body or body part has been warmed or cooled to much and iii) a controller which receives signals from the monitor and is programmed and operative to alter the rate or amount of warming or cooling if a signal received from the monitor indicates that an undesirable symptom or undesirable change in a clinical variable has occurred. Such systems may be used during rewarming of a subject after a period of therapeutic hypothermia or recooling a subject after a period of therapeutic hyperthermia for treatment of a disorder. In such cases, the monitor may monitor for reoccurrence of a symptom of the original disorder or change in a clinical variable that indicates that the therapeutic hypothermia or hyperthermia should be continued for a further period of time. In other applications, the monitor may be used to monitor for the occurrence of a symptom or change in a clinical variable that indicates that continued cooling or warming at the current rate is unsafe or potentially deleterious to the subject. In such cases, the controller may be programmed to delay further cooling or warming or to alter the rate of cooling or warming in response to signals received from the monitor indicating that a symptom or change in a clinical variable that indicates that continued cooling or warming at the current rate is unsafe or potentially deleterious has occurred.

Further aspects and details of the present invention will be understood by those of skill in the relevant art upon reading of the detailed description and examples set forth herebelow.

DETAILED DESCRIPTION AND EXAMPLES

The following detailed description is provided for the purpose of describing only selected embodiments or examples of the invention and is not intended to describe all possible embodiments and examples of the invention.

Figure 1:
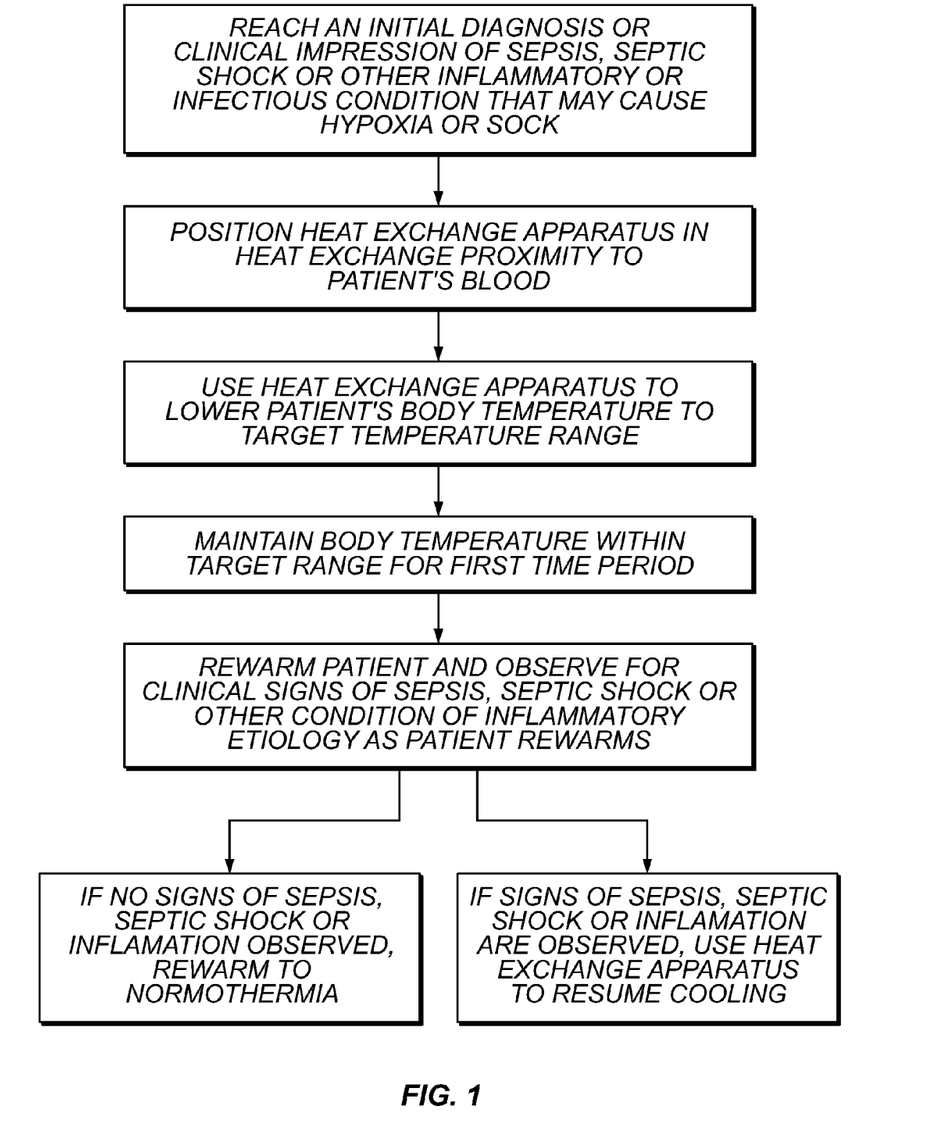
FIG. 1 is a flow diagram showing steps in one method for treating sepsis in accordance with the present invention.

A. A Example of a Method for Treatment of Sepsis, Septic Shock or Other Inflammatory/Infectious Disorder:

FIG. 1 is a flow diagram which shows an example of a method for the use of hypothermia to treat sepsis, septic shock or other inflammatory or infectious disorders that cause tissue/organ hypoxia or shock. In the first step of the example of FIG. 14, an initial diagnosis or clinical impression of actual or impending sepsis, septic shock or other inflammatory or infectious disorders that cause tissue/organ hypoxia or shock is reached. Such diagnosis or clinical impression may be reached on the basis of physical examination and/or patient history and/or laboratory tests. In some patients, a clinical impression that the patient is infected with an antibiotic-resistant microbe (with or without confirming microbiological culture data) may give rise to a clinical impression that the patient is likely to develop sepsis or septic shock.

Figure 2:
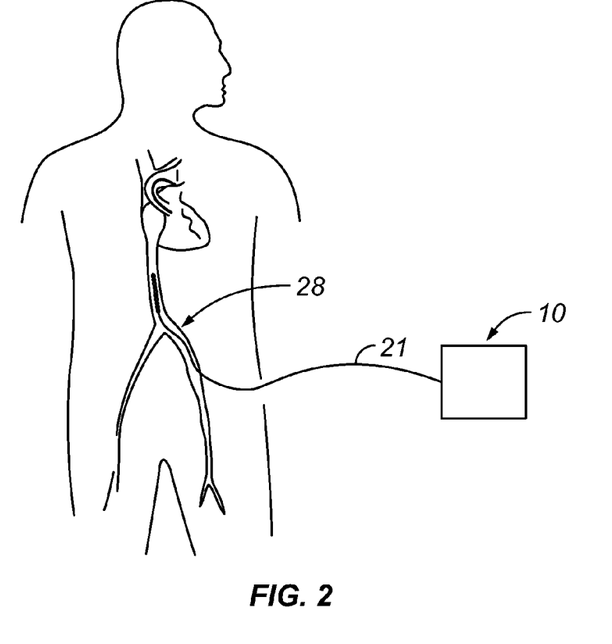
FIG. 2 is a diagram of a human subject having an endovascular heat exchange catheter inserted in the inferior vena cava for treatment of sepsis in accordance with the present invention.
Figure 3:
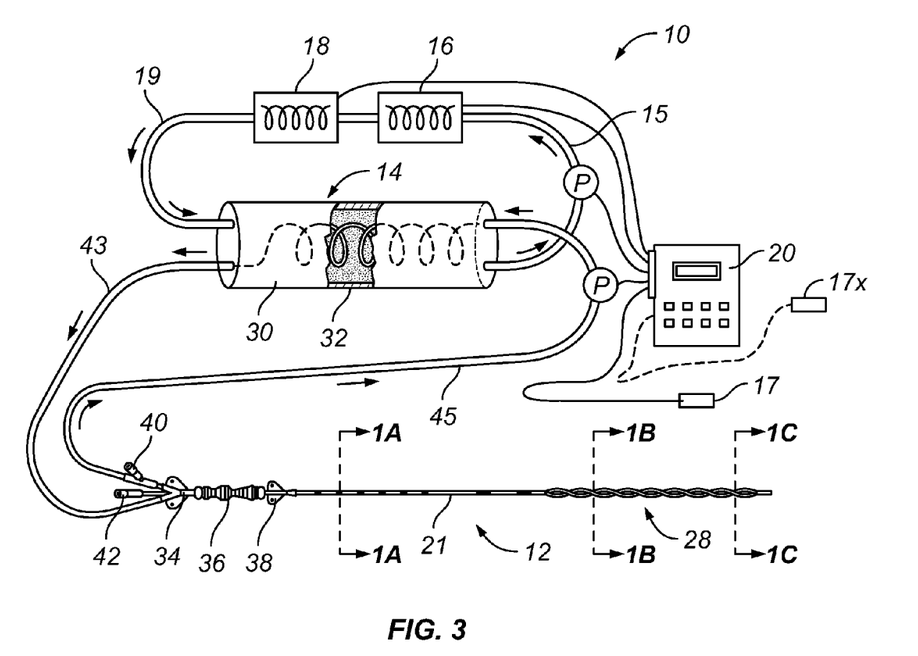
FIG. 3 is a schematic diagram of an endovascular temperature control system of the present invention.

After it has been determined that the patient suffers from actual or impending sepsis, septic shock or other inflammatory or infectious disorders that cause tissue/organ hypoxia or shock, the second step of this method is to position a heat exchange apparatus in heat exchanging proximity with the blood of the patient. This step may be accomplished, as described herein, with any suitable intracorporeal or extracorporeal apparatus for exchanging heat with the patient's blood. For example, a heat exchange catheter, heat exchange probe or other or heat exchanging apparatus may be positioned within a blood vessel, for example the inferior vena cava (IVC), so as to exchange heat with the blood flowing through that blood vessel. FIGS. 1-3, which are described in detail herebelow, show one non-limiting example of an endovascular heat exchange catheter system that is useable in this invention. However, it will be appreciated that various other endovascular heat exchange apparatus may be employed. In general, examples of heat exchange catheters and related devices & controllers that are useable in this step of the method are described in PCT International Application No. PCT/US99/18939 and U.S. Pat. No. 5,486,208 (Ginsburg), U.S. Pat. No. 5,149,676 (Ginsburg), U.S. Pat. No. 6,149,673 (Ginsburg), U.S. Pat. No. 5,174,285 (Fontenot), U.S. Pat. No. 5,344,436 (Fontenot, et al.), U.S. Pat. No. 5,957,963(Dobakl II), U.S. Pat. No. 6,096,608(Dobak II, et al.) and U.S. Pat. No. 6,126,684(Gobin, et al.), the entire disclosures of which expressly incorporated herein by reference. Alternatively, the patient's blood could be circulated through an extracorporeal heat exchange device and then returned to the patient's body.

With further reference to FIG. 1, the third step of the method of this example method may be to use a heat exchange apparatus to cool the patient's blood and/or body temperature to a temperature at which inhibition of inflammation and/or lowered oxygen demand of tissues and/or organs occurs. Typically, in human patients, this step may involve cooling of the patient's blood until the patient's core body temperature has been lowered to 32-34° C., irrespective of whether the patient is initially febrile (>37° C.), normothermic (37° C.) or mildly hypothermic (<36° C.).

Inflammatory processes induced by sepsis trigger a cascade of activation of neutrophils and endothelial cells, increased vascular permeability, enhanced platelet aggregation, and direct effects on metabolic activity. The result is a systemic microcirculatory abnormality leading to an imbalance between systemic oxygen delivery and oxygen demand, which causes global tissue hypoxia, shock, multiorgan failure, and death. After numerous failed clinical trials to affect outcome in sepsis, success has been demonstrated recently with recombinant human activated protein C, a potent antithrombotic and anti-inflammatory mediator. Early goal directed therapy (at the time of presentation prior to arrival in the intensive care unit) with adjustments of cardiac preload, afterload, and contractility to balance oxygen delivery to demand has also recently been shown to improve outcome.

There are several potential beneficial mechanisms associated with hypothermia. Mild hypothermia has been shown to inhibit inflammation; inhibit platelet activation and aggregation; lower metabolism, thus improving the supply demand imbalance associated with tissue hypoxia; and increase myocardial contractility, without increasing myocardial oxygen consumption.

After the patient's body temperature has been cooled to the target temperature, the next step in the method is to maintain the patient's body temperature within a desired range (e.g., 32-34° C.). for a first time period. The length of this first time period may be selected arbitrarily (e.g., 24 hours, 48 hours, 36 hours, etc.) or may be selected based on clinical criteria, such as the severity of the underlying infection or inflammation, the particular pathogen known or suspected to have caused the underlying infection, clinical or laboratory evidence that the underlying infection or inflammatory condition, or circulatory hemodynamics have improved Referring further to the flow diagram of FIG. 1, after the patient's body temperature has been maintained within the target temperature range for the first time period, the next step in the method is to begin to re-warm the patient while observing and/or monitoring for signs that the sepsis, septic shock or other inflammatory condition still exists as to warrant continued hypothermia. In at least some cases, this re-warming of the patient may be carried out using the same heat exchange device that was used to previously cool the patient. If no signs warranting continued hypothermia are observed, the patient's body temperature may be rewarmed to normothermia and the heat exchange device may be removed after the patient has exhibited, for a sufficient period of time, that continued hypothermia is no longer required or indicated. On the other hand, if signs warranting continued hypothermia are observed, the heat exchange device may be used to re-cool the patient to the target hypothemic temperature (e.g., below about 35° C.) or to a temperature within the target range (e.g., between about 32° C. and about 34° C.). The patient's body temperature will then be maintained at such target temperature (or within such target temperature range) for a second time period, after which the re-warming/observation process will be repeated. The re-cooling/maintenance/re-warming & observation may be repeated any number of times until no signs warranting continued hypothermia are observed during the re-warming process.

In patients being treated for septic shock, the types of variables that may measured and/or continually or periodically monitored to determine whether to continued hypothermia is warranted may include any of the above-described symptoms of septic shock such as fever, tachypnea, tachycardia, hypotension, etc. Also, other variables may be measured or monitored and used (individually or in combination) as the basis for deciding whether to continue re-warming the patient or return to hypothermia. For example, decreased mixed venous oxygen saturation ($SvO_2$) (or alternatively a decrease in the partial pressure of oxygen in mixed venous blood) is generally believed to be indicative of septic shock and multiple organ disfunction. $SvO_2$ can be continuously monitored by insertion of catheter having an oxymetry electrode in the patient's pulmonary artery so as to measure oxygen saturation in mixed venous blood flowing through the pulmonary artery. Also, septic shock can be associated with significant increases in cardiac output. Cardiac output can be measured by a number of techniques well known in the art, including continuous measurement of cardiac output by placement of a flow sensing catheter in the patient's pulmonary artery. One example of a pulmonary artery catheter that is suitable for continuous, real time monitoring of both $SvO_2$ and cardiac output is the Swan-Ganz CCOmbo™ Pulmonary Artery Catheter available from Edwards Lifesciences Corporation, Irvine, Calif. Also, non-invasively monitored conjunctival oxygen tension ($PcjO_2$) has been reported to correlate to changes in $SvO_2$ in an experimental animal model of septic shock. Van der Linden, J., Modig, J and Wiklund, L.; Conjunctival Oxygen Tension Monitoring in Experimental Septic Shock; Journal of Clinical Monitoring and Computing; Vol. 6, No. 1, pp. 37-43 (1989).

Another clinical variable that may be indicative of septic shock and multiple organ disfunction is serum lactate concentration. Elevated lactate levels in urine have also been shown to correlate to increased lactate levels in blood in patients suffering from Type I glycogen storage disease. Hagen, T., Korson, M. S. and Wolfsdorf, J. L.; Urinary Lactate Excretion to Monitor the Efficacy of Treatment of Type I Glycogen Storage Disease; 1: Mol Genet Metab. Vol. 70, No. 3, pp. 189-95 (2000). Thus, lactate concentration in blood, urine (or possibly other body fluids) may also be monitored as an indicator of the severity of sepsis or septic shock.

Also, elevated plasma cortisol levels have been associated with septic shock in some patients. Adrenal insufficiency believed to occur in approximately 30% of patients with sepsis or septic shock. Adrenal insufficiency is diagnosed with a cosyntropin stimulation test, which is performed by measuring the response to a dose of adrenocorticotropic hormone (cosyntropin 250 mcg, i.v.) after 30 and 60 minutes. An increase in plasma cortisol of less than 9 mcg/dL is considered to indicate adrenal insufficiency.

Nitric oxide or nitrate levels in the patient's blood may also be indicative of the onset or severity of septic shock. In septic shock, the elaboration of certain cytokines and prostaglandins are believed to cause an increase in endothelial-derived nitric oxide. Nitric oxide causes changes in cell wall transport mechanisms and in intracellular factors, which lead to a decrease in intracellular calcium and subsequently vasodilatation as well as resistance to vasopressor agents. Thus, monitoring of nitric oxide or nitrate levels in the patient's blood may provide an indication of the onset or severity of septic shock. For example, an elevated plasma nitrate level (e.g., above 100 µmol/l) in a patient with circulatory shock of unclear origin has been reported to be a reliable indicator of a septic origin.

Also, various other cellular and/or humoral mediators of sepsis or septic shock may also be measured or continuously monitored and used as bases for deciding whether continued hypothermic therapy is indicated.

Figure 2A:
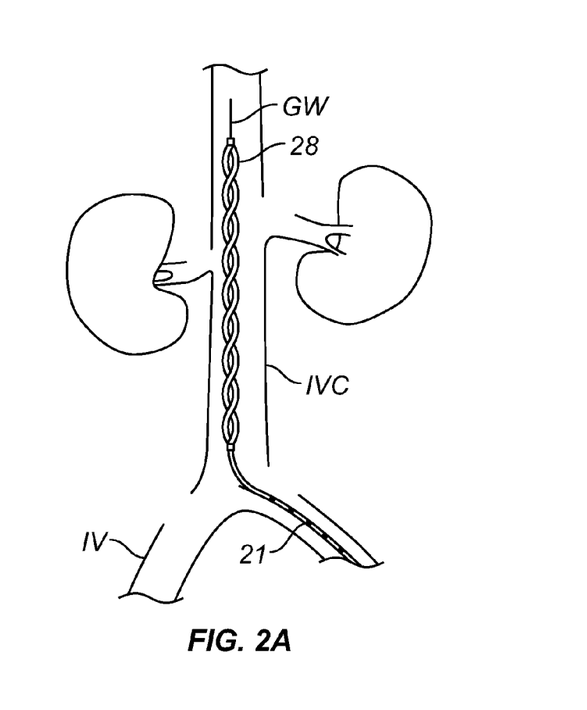
FIG. 2A is an enlarged view of the inferior vena cava of the human subject shown in FIG. 2 showing the heat exchange catheter inserted therein.

The use of an endovascular heat exchange apparatus such as as the heat exchange catheter shown in FIGS. 2-3 and described herebelow may permit hypothermia to be induced more rapidly and with substantially greater control than by noninvasive means such as wrapping the patient in a hypothermia blanket. The target temperature to which the patient is initially cooled will typically be below about 35° C., and preferably in the range of approximately 32° C. to approximately 34° C. In this invention, either whole-body hypothermia or partial-body hypothermia may be used. When whole-body hypothermia is used, the patient=s core body temperature may be monitored and maintained at the desired target temperature for the first time period. When partial-body hypothermia is used the temperature of a desired organ, limb or anatomical portion of the body will be monitored and maintained at the desired temperature or within the desired temperature range. Concurrently with the hypothermia, the patient may be anesthetized or may receive medications or other therapy to prevent or lessen shivering or discomfort due to the hypothermia. Examples of medications that may be administered to minimize shivering or discomfort during the hypothermic treatment are described in PCT International Application No. PCT/US00/20321. The specific drugs used to prevent shivering may include meperidine, buspirome, dexmedetomidine and/or combinations thereof. In the alternative, in some where it is undesirable to administer anti-shivering drugs, the patient=s body temperature may be lowered somewhat (to achieve at least some of the desired therapeutic effect) but maintained above the shivering threshold, which shivering threshold is typically encountered in human patients at core body temperatures between 35° C. and 35.5° C.

Hypothermia may be administered as the sole treatment, at least for a period of time sufficient to allow physicians to fully evaluate the patient=s condition and to treat the infection or other underlying condition. In some cases, it may be desirable to administer hypothermia in accordance with this invention concurrently with the administration of other treatments for the underlying sepsis, septic shock or other systemic inflammatory or infectious condition. In cases of sepsis or septic shock, examples of other treatments that may be combined with the hypothermic treatment of the present invention include, but are not limited to; administration of antibiotics or antimicrobial agents, administration of steroids or other anti-inflammatory agents, antithrombotic agents, hydration, maintenance of electrolyte and acid/base balance, mechanical ventilation, chest physical therapy/suction to ameliorate lung congestion, etc. The application of hypothermia in accordance with this invention may, in addition to inhibiting systemic inflammation, simultaneously reduce overall tissue and/or organ damage to hypoxia and/or decreased circulation. For example, the application of hypothermia may, simultaneously with reduction of systemic inflammation, lower the metabolic rate and oxygen demand of organs or tissues that may be starved for oxygen due to the hypoxic and/or circulatory effects associated with the patient's condition. In this regard, hypothermia has been found to be generally myoprotective (i.e., protective of muscle cells against damage from insults like hypothermia or ischemia) and if intravascular hypothermia is applied to the blood in the IVC immediately before the blood enters the heart, it might simultaneously provide protection against damage to or infarction of the myocardium. Likewise, hypothermia has been shown to be generally neuroportective, and may protect the brain tissue against hypoxic or ischemic damage as may occur in septic shock and other shock states.

The methods of the present invention are not limited to use in the treatment of sepsis, septic shock or systemic inflammation. Rather, the present invention also includes general methods wherein warming or cooling all or a portion of the body is carried out using an endovascular heat exchange catheter as described above and wherein a monitor (e.g., a sensor or other suitable monitoring apparatus) is used to monitor for the occurrence of an undesirable symptom or undesirable change in a clinical variable (e.g., a physiologic variable, biochemical variable, physical change, etc.) which indicates that the rate of warming or cooling is to rapid (or has commenced too soon) or that the body or body part has been warmed or cooled to much. If such a symptom or change on a clinical variable is observed, remedial action (e.g., reversing the cooling or warming, leveling off and maintaining the current temperature or adjusting the rate of the cooling or warming) is taken. In some cases, the symptom or change in a clinical variable may be the reoccurrence during rewarming or recooling of a symptom or sign of an original disorder for which the subject was originally being treated by therapeutic hypothermia or hyperthermia. In other cases, the symptom or change in clinical variable may be occurrence of some other untoward or undesired effect associated with the warming or cooling process. The present invention further includes systems for carrying out these methods, such systems comprising (i) a heat exchange catheter that is insertable into the subject's vasculature and useable to warm or cool blood flowing through the subject's vasculature, thereby warming or cooling all or a portion of the subject's body, ii) a monitor (e.g., a sensor) which monitors for the occurrence of an undesirable symptom or undesirable change in a clinical variable which indicates that the rate of warming or cooling is to rapid or that the body or body part has been warmed or cooled to much and iii) a controller which receives signals from the monitor and is programmed and operative to alter the rate or amount of warming or cooling if a signal received from the monitor indicates that an undesirable symptom or undesirable change in a clinical variable has occurred. Such systems may be used during rewarming of a subject after a period of therapeutic hypothermia or recooling a subject after a period of therapeutic hyperthermia for treatment of a disorder. In such cases, the monitor may monitor for reoccurrence of a symptom of the original disorder or change in a clinical variable that indicates that the therapeutic hypothermia or hyperthermia should be continued for a further period of time. In other applications, the monitor may be used to monitor for the occurrence of a symptom or change in a clinical variable that indicates that continued cooling or warming at the current rate is unsafe or potentially deleterious to the subject. In such cases, the controller may be programmed to delay further cooling or warming or to alter the rate of cooling or warming in response to signals received from the monitor indicating that a symptom or change in a clinical variable that indicates that continued cooling or warming at the current rate is unsafe or potentially deleterious has occurred.

For example, when hypothermic patients are being rewarmed, they can sometimes exhibit sinus reversible electrogardiographic changes such as bradycardia, primary AV block, widened QRS complex with Osborne waves and QT prolongation. Markus, L., et al.; *Reversible Electrocardiographic Changes In Hypothermia*; Zeitschrift fur Kardiologie; Vol. 93, No. 8, pp. 630-33 (August 2004). In at least some cases, when one or more of these undesirable electrocardiographic changes are observed, it may be desirable to adjust the rate of rewarming, hold at the current body temperatue or even re-lower the subject's body temperature by some desired amount, or to otherwise take remedial action in view of the occurrence of such undesirable change n the subject's electrocardiogram.

Also, the present invention includes generally methods and systems wherein an endovascular heat exchange system of the type described herein is used to warm or cool all or a portion of a subject's body and a monitor is used to monitor for some desirable symptom or change in a clinical variable. In response, further cooling or warming may be stopped and the subject's body temperature may be maintained at that body temperature for some desired period of time. For example, if the subject is being cooled or warmed to treat a particular disorder, the monitor may monitor for a desired cessation or diminution of a symptom of that disorder and, when that desired cessation or diminution of a symptom has occurred, the subject's body temperature may be maintained at its then-current temperature for some desired period of time before rewarming or recooling is attempted. Similarly, if the monitor indicates that the symptoms of the original disorder recommence or become more sever, further cooling or warming may be effected in response to that observation.

B. An Example of an Intravascular Heat Exchange Catheter System
Useable in this Invention FIGS. 2 through 3 generally show one example of an heat exchange catheter system 10 of the present invention. Further details of this heat exchange catheter system 10, except for the below-described sensors for monitoring variables indicating sepsis or septic shock and the feedback control relating thereto, are described in U.S. patent application Ser. No. 11/479,961 entitled Devices, Systems and Methods for Rapid Endovascular Cooling filed Jun. 29, 2006, which is expressly incorporated herein by reference. In this example, the heat exchange catheter system 10 generally comprises a) a heat exchange catheter 12, b) an extracorporeal heat exchanger 14, c) a cooler 16 and/or heater 18, d) a body temperature measuring apparatus 17 and e) a programmable controller 20. In some instances, a cooler 16 and heater 18 may be combined or integrated into a single apparatus that alternately heats and cools (e.g., a thermoelectric cooler/heater) while in other instances a separate cooler 16 (e.g., a refrigerator, condenser, thermoelectric cooler, mass of cold matter, etc) and/or separate heater (e.g., a resistance heater, thermoelectric heater, mass of warm matter, etc.) may be used.

Figure 3A:
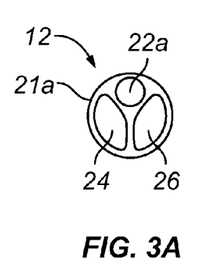
FIG. 3A is a cross sectional view through line 3A-3A of FIG. 3.

As may be appreciated from the showings of FIGS. 2A and 3, the heat exchange catheter 12 generally comprises an elongate catheter body 21 having an intracorporeal heat exchanger 28 mounted thereon. As shown in the cross section of FIG. 3A, a proximal portion of the catheter comprises a proximal shaft 21a having a first thermal exchange fluid lumen 24, a second thermal exchange fluid lumen 26 and a working lumen 22a. At or near the distal end of the proximal shaft 21a the first thermal exchange fluid lumen 24 terminates and communicates through openings into three generally cylindrical balloon lobes 29a, 29b and 29c such that thermal exchange fluid may flow out of proximal portions of the balloon lobes 29a, 29b and 29c and into the first thermal exchange fluid lumen 24. Thus, in this particular example, the first thermal exchange fluid lumen 24 carries outflow of the thermal exchange fluid from the intracorporeal heat exchanger 28 back toward the extracorporeal heat exchanger.

Figure 3B:
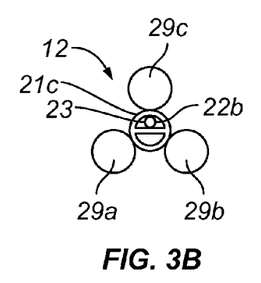
FIG. 3B is a cross sectional view through line 3B-3B of FIG. 3.

As seen in the cross section of FIG. 3B, balloon lobes 29a, 29b and 29c are twisted, wound or otherwise helically disposed about a mid-portion 21b of the catheter shaft. In this example, the mid-portion 21b of the catheter shaft comprises a continuation or extension of the second thermal exchange fluid lumen 26 along with a smaller tube 23 having a lumen 22b that is connected to and forms a continuation or extension of the proximal working lumen 22a. The balloon lobes 29a, 29b and 29c and the second thermal exchange fluid lumen 26 terminate at the distal end of the mid-portion 21b of the catheter shaft. Also at or near the distal end of the mid-portion 21b of the catheter shaft the second thermal exchange fluid lumen 26 terminates and communicates through openings into three generally cylindrical balloon lobes 29a, 29b and 29c such that thermal exchange fluid may flow from the second thermal exchange fluid lumen 26 and into distal portions of the balloon lobes 29a, 29b and 29c. Thus, in this example, the second thermal exchange fluid lumen 26 carries inflow of the thermal exchange fluid to the intracorporeal heat exchanger 28. The attachment of the balloon lobes to the catheter may be accomplished in any appropriate manner to accomplish the circulation of heat exchange fluid described here. One such method is described in detail in U.S. Pat. No. 6,610,083 (Keller, et al.), which patent is expressly incorporated herein by reference.

Figure 3C:
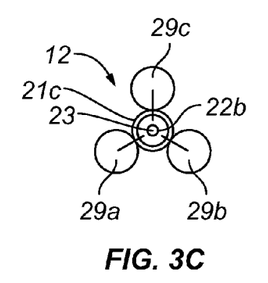
FIG. 3C is a cross sectional view through line 3C-3C of FIG. 3.

As shown in the cross section of FIG. 3C, a distal portion 21c of the catheter shaft extends beyond the distal ends of the balloon lobes 29a, 29b and 29c. Tube 23 having working lumen 22b continues through this distal portion 21c of the catheter shaft and its lumen 22b opens through an aperture in the distal tip of the catheter 12. Thus, in this manner, the working lumen 22a of the proximal catheter shaft 21a and working lumen 22b of the mid-portion and distal catheter shafts 21b, 21c combine to form a continuous working lumen that extends through the shaft 21 of the heat exchange catheter 12. In some embodiments, a working lumen that runs less than the entire length of the catheter shaft 21 may be provided to facilitate rapid exchange of guidewires and/or catheters. As those of skill in the art will appreciate, such working lumen 22a, 22b may facilitate advancement of the catheter 12 over a guidewire and/or to facilitate infusion of fluids (e.g., saline solution, therapeutic or diagnostic substances, radiographic contrast medium, aqueous oxygen, etc.) and/or to facilitate introduction of another catheter or apparatus into the subject's body. One example of another apparatus that may be advanced through the working lumen 22a, 22b is an endovascular embodiment of the body temperature measuring apparatus 17 (e.g., a catheter or wire having a temperature sensor that is advanceable out of the distal tip of the catheter 12 or shaft 21 and useable for sensing the temperature of the subject's flowing blood). One example of an endovascular embodiment of the body temperature measuring apparatus 17 that may be advanced through working lumen 22a, 22b is the Reprieve® endovascular temperature probe manufactured by Radiant Medical, Inc., Redwood City, Calif.

As shown in FIG. 1, the proximal end of the catheter shaft 21 may be provided with a generally tubular, flexible sterility barrier 36 disposed between proximal hub 34 and distal hub 38. The catheter shaft 21 may be slideably advanced and retracted through the distal hub 38 while the proximal hub 34 is affixed in a substantially stationary manner to the catheter shaft 21. The distal hub 38 may be affixed to the subject's skin by sutures, adhesive or other means, at a location immediately adjacent to the location where the catheter shaft 21 enters percutaneously into the subject's body. At the time of initial insertion, the catheter shaft 21 is advanced into the subject's body to a desired initial position. In some applications, the specific positioning of the intracorporeal heat exchanger 28 within the body may affect the efficiency and rapidity with which the intracorporeal heat exchanger 28 heats or cools the subject's body. In this regard, some heat exchange catheters 12 of the present invention may include optional elements useable to facilitate positioning of the entire intracorporeal heat exchanger 28 at a desired position within the body (e.g., within the inferior vena cava). Examples of such optional elements are shown in FIGS. 4A-4D and described fully hereinbelow. After the catheter shaft 21 has been advanced to its desired initial position, the proximal and distal hubs are affixed to the subject's skin such that the sterility barrier 36 encases and maintains sterility of the exteriorized portion of the catheter shaft 21. At a later time if it is desired to adjust the position of the catheter 12, the proximal hub 34 may be detached from the subject's body and the catheter shaft may be further advanced or retracted, as needed, through the distal hub 38. When the desired repositioning of the catheter 12 has been achieved, the proximal hub 34 may one again be affixed to the subject's body and the sterility barrier 36 will continue to shield the exteriorized portion of the catheter shaft 21 from contamination. Further details and examples of this arrangement as well as other valving systems and other elements that may be incorporated into the proximal end of the catheter device 12 are described in U.S. Pat. No. 6,887,263 (Bleam et al.) which is expressly incorporated herein by reference.

A valved port 42, such as tube having a Tuohy-Borst valve, is attached to the proximal end of the proximal working lumen 22a to facilitate advancement of a guidewire, infusion of fluids (e.g., saline solution, therapeutic or diagnostic substances, radiographic contrast medium, etc.) or introduction of other catheter or apparatus into the subject's body through working lumen 22a, 22b.

A second valved port 40, such as a such as Y tube having a stopcock on one arm thereof, is attached to the proximal end of the first thermal exchange lumen 24 to facilitate venting or purging or air or unwanted fluid from the system during the initial filling of the system with thermal exchange fluid.

With reference to FIG. 1, the extracorporeal heat exchanger 14 comprises a shell 30 having an inner tube 32 extending therethrough. Outflow tube 45 connects the first thermal exchange lumen 24 to the inlet of the inner tube 32 and inflow tube 43 connects the outlet of the inner tube 32 to the second thermal exchange lumen 26. Thermal exchange fluid is thus pumped from the inner tube 32 of the extracorporeal heat exchanger 14, through the second (inflow) thermal exchange lumen 26, into the distal portions of balloon lobes 29a, 29b, 29c, through the balloon lobes 29a, 29b, 29c in the proximal direction, into the first (outflow) thermal exchange lumen 24, through tube 45 and back into the inner tube 32 of the extracorporeal heat exchanger 14. Tube 15 connects an outlet from the shell 30 of extracorporeal heat exchanger 14 to cooler 16 and/or heater 18. Tube 19 connects the cooler 16 and/or heater 18 to an inlet of the shell 30 of extracorporeal heat exchanger 14. Thus, heated or cooled fluid (e.g., a glycol such as propylene glycol or other suitable thermal exchange fluid) circulates from the cooler 16 and/or heater 18, through tube 19, through the shell 30 of extracorporeal heat exchanger 14, through tube 15 and again through cooler 16 and/or heater 18.

The operator inputs into the controller 20 a target body temperature. The controller 20 is in communication with the body temperature measuring apparatus 17 and receives signals indicative of the temperature of all or a portion of the subject's body. The controller 20 controls one or more of: a) the operation of the cooler 16 and/or heater 18, b) the flowrate of the heated or cooled fluid through the extracorporeal heat exchanger, c) the flowrate of thermal exchange fluid through the extracorporeal heat exchanger 14, and/or the flowrate of thermal exchange fluid through the intracorporeal heat exchanger 28, thereby causing the subject's body to be cooled or warmed to the desired target body temperature and maintaining such target body temperature for a desired period of time. Additionally, in at least some embodiments, the controller 20 may be programmed to effect a rewarming procedure after the subject's body temperature has been maintained at the target temperature for a first time period (see method flow diagram of FIG. 1). In this regard, the system 10 may include a keyboard or other apparatus for the operator to input a command to commence a rewarming process. When such rewarming process is commenced, the controller 20 will continually, or in stepwise fashion, raise the temperature of the heat exchange fluid being circulated through the intracorporeal heat exchanger 28 so as to raise the subject's body temperature. Continuously or at selected time points during such rewarming process, one or more variables may be measured or monitored to determine whether the subject is exhibiting signs of continuing sepsis or septic shock that would warrant recooling and continued hypothermia, or whether the septic shock appears to have been to have subsided so that rewarming of the subject's body to normothermia may be continued. Such measuring or monitoring of variable(s) may be performed manually or, in some cases, the system 10 may include one or more additional sensor(s) 17x which will measure or monitor one or more variable(s) that indicate whether recooling and continued hypothermia, or whether the septic shock appears to have been to have subsided so that rewarming of the subject's body to normothermia may be continued. In embodiments that include such additional sensor(s) 17x, the additional sensor(s) 17x may communicate the measured or monitored variable(s) to the controller 20 and the controller may be further programmed to compare such measured or monitored variable(s) with preprogrammed acceptable parameters and, on that basis, to either a) continue rewarming the subject or b) recool the patient and continue the hypothermia for a second time period. As described above, the types of variable(s) the additional sensor(s) 17x may measure or monitor include but are not limited to heart rate, respiratory rate, arterial blood pressure, venous oxygen saturation ($SvO_2$) (or alternatively the partial pressure of oxygen in mixed venous blood), conjunctival oxygen tension ($PcjO_2$), lactate concentration in blood, urine or other body fluids and/or other cellular or humoral indicators of sepsis or septic shock. In this example, the additional sensor(s) $17x$ may comprise a pulmonary artery catheter that is equipped for continuous monitoring of both $SvO_2$ and cardiac output (e.g., the Swan-Ganz CCOmbo™ Pulmonary Artery Catheter available from Edwards Lifesciences Corporation, Irvine, Calif.) and the controller 20 is programmed to receive the monitored $SvO_2$ and cardiac output data from the sensor $17x$ and to determine if and when the monitored $SvO_2$ and cardiac output data indicates that the subject remains in septic shock. For example, rewarming should not continue if 1) cardiac index falls below 3 l/min/m$^2$ or if $SvO_2$ falls below 70%, or lactate rises >4 mmol/l (36 mg/dl), or if mean arterial pressure, MAP, falls below 65 mm Hg. If, during the rewarming process, the controller 20 determines that the monitored $SvO_2$ and cardiac output data indicates that the subject continues to suffer from treatable septic shock, the controller may then be programmed to automatically reset to the original target temperature (or some other temperature that is incrementally lower than the present body temperature) so as to cause the subject's body temperature to again be lowered and maintained at such lowered body temperature for a second time period or until such time as the operator again inputs an instruction to begin the rewarming process. The rewarming profile can be set for continuous slow rate of 0.1 to 0.5 C per hour.

During initial insertion of the catheter 12, the balloon lobes 29a, 29b, 29c are deflated and collapsed to a low profile that is the same or only slightly larger in diameter than the adjacent catheter shaft 21. After the catheter 12 has been inserted into the subject's vasculature, the thermal exchange fluid is allowed to flow into the balloon lobes 29a, 29b, 29c, thereby causing the lobes to inflate or expand. (The lobes "inflate" in the sense that they become substantially filled with liquid and take on their full expanded size and shape. However, it is to be appreciated that in at least some embodiments the lobes may be non-compliant or semi-compliant (e.g., polyethylene theaphthalate (PET) or Nylon) balloons with a wall thickness of between 0.00040 inches and 0.00065 inches.) Thus, the intracorporeal heat exchanger 28 has a balloon with a first circumscribed diameter $D_1$ when the balloon lobes 29a, 29b, 29c are empty and collapsed and a second circumscribed diameter $D_2$ when the balloon lobes 29a, 29b, 29c are fully filled and inflated. It is desirable that the first circumscribed diameter $D_1$ be small enough to allow the catheter 12 to be inserted through a vascular introducer of a desired size. Additionally, the efficiency or rapidity of heat exchange is directly affected by a number of factors, one of which is the blood-contacting surface area of the inflated balloon lobes 29a, 29b, 29c. Essentially, the greater the blood contacting surface area of the balloon lobes 29a, 29b, 29c, the greater the efficiency and rapidity of blood cooling or warming. However, the second circumscribed diameter $D_2$ should typically be smaller than the diameter of the blood vessel lumen in which the intracorporeal heat exchanger 28 is positioned so and not to substantially obstruct the flow of blood through that blood vessel lumen. An advantage of the multi-lobed balloon 28 of the present invention over intravascular heat exchange balloons of the prior art is that the heat exchange balloon 28 of the present invention may be expanded within a vessel to a second circumscribed diameter D2 that near or equal to the luminal diameter of the vessel but the resultant blockage of cross-sectional area of the vessel's lumen is limited to approximately 50% due to the sizing of the lobes 29a, 29b, 29c and the presence of flow path(s) between the lobes 29a, 29b, 29c. This is comparable with in vivo testing of the Greenfield IVC filter, a conical shaped screen type device where blockages equivalent to 64% of cross-sectional area have occurred without development of a pressure gradient across the filter.

In applications, such as that shown in FIGS. 2 and 2A, where the catheter is to be inserted into the femoral vein and advanced to a position within the inferior vena cava, use of a vascular introducer no larger than 12 to 14 French will be desired. Thus, in embodiments intended for femoral insertion, it is preferable that the first circumscribed diameter $D_1$ be less than about 4.7 mm, or in some cases less than about 4.5 mm, or otherwise sized to fit through a 14 French or smaller vascular introducer. The lumen of the inferior vena cava of an adult human typically has an average diameter of 20-22 mm. Thus, to maximize efficiency and/or rapidity of cooling or warming while not substantially obstructing blood flow, in embodiments intended for femoral insertion and advancement of the intracorporeal heat exchanger 28 into the inferior vena cava of an adult, it is preferable that the second circumscribed diameter $D_2$ be greater than about 14 mm. Accordingly, in such embodiments of the catheter 12, the second circumscribed diameter $D_2$ will desirably be at least about 3 times greater than the first circumscribed diameter $D_1$.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A system for treating sepsis, septic shock or other inflammatory conditions that give rise to multiple organ disfunction, said system comprising:
   a heat exchange catheter that is insertable into the subject's vasculature so as to exchange heat with blood flowing through the subject's vasculature thereby raising or lowering the subject's body temperature;
   a controller that is programmed to cause, or which receives operator commands to, i) cause the heat exchange catheter to lower the subject's body temperature to lowered temperature, ii) maintain said lowered temperature for a first period of time and iii) subsequently cause the heat exchange catheter to rewarm the subject's body temperature;
   at least one sensor that measures or monitors, during rewarming of the subject's body temperature, at least one variable that indicates whether further hypothermia is desirable, said sensor generating a signal representative of said at least one variable, said signal being transmitted to the controller;

the controller being further programmed to continue rewarming, maintain or relower the subject's body temperature in response to the signal received from the sensor during rewarming.

2. A system according to claim 1 wherein the sensor measures or monitors at least one variable selected from the group consisting of:
- heart rate;
- respiratory rate;
- arterial blood pressure;
- venous oxygen saturation (SvO2);
- partial pressure of oxygen in mixed venous blood;
- conjunctival oxygen tension (PcjO2);
- lactate concentration in blood, serum, urine or other body fluids;
- other cellular or humoral indicators of sepsis or septic shock;
- heart rate above about 100;
- SvO2 below about 70%;
- serum lactate above about 4 mmol/l;
- mean arterial blood pressure below about 65 mm Hg; and
- systolic blood pressure less than about 90 mm Hg.

3. A system according to claim 1 wherein the sensor communicates with the controller and the controller is further programmed to determine whether said at least one variable exceeds a predetermined acceptable limit, indicating that further hypothermia is desirable.

4. A system according to claim 3 wherein the controller is further programmed to provide notification to the operator that said at least one variable has exceeded a predetermined acceptable limit.

5. A system according to claim 3 wherein the controller is further programmed to cause the heat exchange catheter to lower the subject's body temperature upon determining that said at least one variable has exceeded a predetermined acceptable limit during rewarming.

6. A method for warming or cooling all or a portion of the body of a human or animal subject to treat a disorder, said method comprising the steps of:
(A) inserting a heat exchange catheter into the subject's vasculature;
(B) using the heat exchange catheter to warm or cool blood flowing through the subject's vasculature, thereby resulting in warming or cooling of all or a portion of the subject's body;
(C) monitoring at least one symptom or clinical variable related to the disorder; and
(D) controlling at least one operational variable selected from i) the rate of warming or cooling of blood flowing through the subject's vasculature and ii) the temperature to which the subject's body or body portion is warmed or cooled, in response to the monitored symptom or clinical variable;
wherein said at least one symptom or clinical variable is selected from the group consisting of:
- heart rate;
- respiratory rate;
- arterial blood pressure;
- venous oxygen saturation ($SvO_2$);
- partial pressure of oxygen in mixed venous blood;
- conjunctival oxygen tension ($PcjO_2$);
- lactate concentration in blood, serum, urine or other body fluids;
- other cellular or humoral indicators of sepsis or septic shock;
- heart rate above about 100;
- $SvO_2$ below about 70%;
- serum lactate above about 4 mmol/l;
- mean arterial blood pressure below about 65 mm Hg; and
- systolic blood pressure less than about 90 mm Hg.

7. A method according to claim 6 wherein a desired change in said at least one symptom or clinical variable indicates when the warming or cooling is having an intended therapeutic effect and wherein Step D comprises causing the subject's body or body portion to be warmed or cooled to a temperature at which the monitored operational variable indicates that the intended effect has been achieved and thereafter maintaining the subject's body or body portion at or near that temperature for a period of time.

8. A method according to claim 6 wherein the disorder has caused a clinical variable to be outside of a known normal range and wherein the desired change in said in said at least one symptom or clinical variable is when that clinical variable has returned to within the normal range.

9. A method according to claim 6 wherein the disorder causes a symptom to occur and wherein the desired change in said in said at least one symptom or clinical variable is a predetermined amount of diminution or cessation of that symptom.

10. A system for warming or cooling all or a portion of the body of a human or animal subject to treat a disorder, said system comprising:
a heat exchange catheter that is insertable into the subject's vasculature and useable to warm or cool blood flowing through the subject's vasculature, thereby warming or cooling all or a portion of the subject's body;
a temperature sensor for sensing body temperature of the subject;
a symptom or clinical variable monitor for monitoring at least one symptom or clinical variable other than body temperature; and
a controller that is programmed to control the warming or cooling of the subject's body by the heat exchange catheter; and
said controller being further programmed to respond to predetermined changes of a symptom or clinical variable being monitored by the symptom or clinical variable monitor by causing the heat exchange catheter to either switch from cooling to warming for a period of time or switch from warming to cooling for a period of time.

11. A system according to claim 10 wherein the predetermined change comprises either the occurrence or diminution of the symptom or a change in the clinical variable of a magnitude, which indicates that re-cooling or re-warming of the subject's body is desirable.

12. A system according to claim 11 wherein the disorder causes the clinical variable to be outside of a known normal range for that clinical variable and wherein the predetermined change is when the clinical variable becomes within the normal range.

13. A system according to claim 11 wherein the disorder causes the symptom to occur and wherein the predetermined change is a predetermined amount of diminution or cessation of that symptom.

14. A method according to claim 10 wherein the disorder is sepsis or septic shock and wherein said at least one symptom or clinical variable is selected from the group consisting of:
heart rate;

respiratory rate;
arterial blood pressure;
venous oxygen saturation (SvO2);
partial pressure of oxygen in mixed venous blood;
conjunctival oxygen tension (PcjO2);
lactate concentration in blood, serum, urine or other body fluids;
other cellular or humoral indicators of sepsis or septic shock;
heart rate above about 100;
SvO2 below about 70%;
serum lactate above about 4 mmol/l;
mean arterial blood pressure below about 65 mm Hg; and
systolic blood pressure less than about 90 mm Hg.

15. A method for warming or cooling all or a portion of the body of a human or animal subject, said method comprising the steps of:
   inserting a heat exchange catheter into the subject's vasculature;
   positioning on or in the subject's body a first sensor to sense body temperature of the subject;
   positioning on or in the subject's body a second sensor for sensing a symptom or clinical variable other than body temperature which indicates whether the subject's body is exhibiting an undesired effect of the warming or cooling;
   using the heat exchange catheter to warm or cool blood flowing through the subject's vasculature, thereby resulting in warming or cooling of all or a portion of the subject's body;
   using the first sensor to monitor body temperature of the subject;
   using the second sensor to monitor said symptom or clinical variable other than body temperature; and
   either switching from cooling to warming for a period of time or switching from warming to cooling for a period of time, in response to a predetermined change in a symptom or clinical variable monitored by the second sensor.

16. A method according to claim 15 wherein:
   the subject is being warmed;
   the predetermined change in the monitored symptom or clinical variable indicates an undesired effect of the warming; and
   in response, the warming is terminated and cooling is initiated.

17. A method according to claim 16 wherein the predetermined change in the monitored symptom or clinical variable comprises an undeired change in the subject's electrocardiogram.

18. A method according to claim 16 wherein:
   the subject is being cooled;
   the predetermined change in the monitored symptom or clinical variable indicates an undesired effect of the cooling; and
   in response, the cooling is terminated and warming is initiated.

19. A method according to claim 18 wherein the predetermined change in the monitored symptom or clinical variable comprises an undesired change in the subject's electrocardiogram.

* * * * *